United States Patent
Andrews et al.

(10) Patent No.: US 6,456,955 B1
(45) Date of Patent: Sep. 24, 2002

(54) AUTOMATED TEST PROTOCOL

(75) Inventors: Richard Wayne Andrews, Rehoboth; Virginia L. Corbin, Medway, both of MA (US)

(73) Assignee: Waters Investments Limited

( * ) Notice: Subject to any disclaimer, the term of this patent is extended or adjusted under 35 U.S.C. 154(b) by 47 days.

(21) Appl. No.: 09/730,126

(22) Filed: Dec. 5, 2000

(51) Int. Cl.$^7$ .................. G01N 37/00; B01D 15/08; G06F 19/00

(52) U.S. Cl. .................. 702/104; 702/81; 702/84; 210/198.2

(58) Field of Search .................. 702/81, 84, 100, 702/104, 182.183; 417/244, 313; 210/180, 198.2, 656

(56) References Cited

U.S. PATENT DOCUMENTS 5,360,320 A * 11/1994 Jameson et al. .......... 417/4
5,980,742 A * 11/1999 Saitoh .................. 210/198.2
6,228,153 B1 * 5/2001 Saitoh .................. 210/198.2
6,296,771 B1 * 10/2001 Miroslav .................. 210/656

* cited by examiner

Primary Examiner—Bryan Bui
(74) Attorney, Agent, or Firm—Brian Michaelis

(57) ABSTRACT

A method and apparatus for automating the qualification process for chromatographic systems. Automation technology and regression analysis are used for qualifying a chromatography system. The trained operator prepares the chromatography system to ensure that the samples, solvents, and the separation column are ready for analysis. The qualification of the detector, the solvent delivery system, the sample manager, the gradient proportioning system, the column heater, and the delay volume of the chromatography system are completed without the necessity of operator intervention. Regression analysis is performed to compute performance statistics that demonstrate the accuracy, linearity, and precision of the chromatographic system and quantify its suitability for chromatographic analysis.

18 Claims, 13 Drawing Sheets

AUTOMATED TEST PROTOCOL

FIELD OF THE INVENTION

The present invention relates to chromatography systems, and more particularly the use of automation technology in the qualification of chromatography systems.

BACKGROUND OF THE INVENTION

Chromatography systems are used to analyze various products developed by pharmaceutical companies, hospitals, and government laboratories. Such products in many cases are regulated by the United States Food and Drug Administration (the "FDA") and other foreign regulatory agencies, therefore regulatory guidelines require the validation of these chromatography systems for laboratories submitting data, e.g. pharmaceutical samples to the above regulatory agencies. The regulatory requirements demand that the chromatography systems that are used to analyze products must meet certain minimum requirements as many regulatory agencies will not accept data from laboratories that have not established that they are using validated chromatography systems.

When a chromatography system satisfies the validation requirements, it is said to be "qualified". A qualified chromatography system generally must meet the articulated standards in three separate areas. The three areas are installation, operation, and performance. Each area is described below.

The installation qualification ("IQ") verifies that the chromatography system satisfies three conditions associated with the installation of the system. First, the IQ establishes the chromatography system is received as designed. Second, it verifies the chromatography system is installed properly. Lastly, the IQ verifies that the environment where the system is installed is appropriate.

The operational qualification ("OQ") ensures the instruments which comprise the chromatography system function according to their individual operational specifications in the chosen environment. An OQ does not specifically verify that individual modules successfully perform as part of an integrated system.

The performance qualification ("PQ") ensures the integrated chromatography system routinely performs according to specification.

Conventional methods for qualifying chromatography systems include manuals, qualification workbooks, and metrology based qualifications. An example is the Waters HPLC Systems Qualification Workbook developed by Waters Corporation of Milford, Massachusetts. This highly manual and labor intensive process takes from 10–12 hours to finish per chromatographic system. Qualification via qualification workbooks is extremely time consuming because the individual modules and the integrated system are qualified separately.

Attempts to automate the qualification systems, such as with the Hewlett Packard 1100, have not been successful. The HP method is merely a manual system with the only improvement being that the workbook for the use of the system is contained on a cd-rom.

Another disadvantage of conventional methods of qualification is that different samples, solvents, and methods are used in the qualification of the modules (OQ) and those used for the qualification of the system (PQ). are different than those used by the lab on a daily basis. Consequently, a significant amount of time is lost in removing solvents and samples from the chromatograph and documenting the multiple reagents and samples used in system qualification. Therefore, conventional methods take too much time and require constant technical human intervention. Because of the demands of continual human intervention, the cost to industry is excessive. Additionally, the need to maintain and retrieve the various qualification reports is burdensome and not amenable to the advantages of electronic format.

SUMMARY OF THE INVENTION

The present invention provides methods and apparatus for automating the qualification process for chromatographic systems.

According to the invention automation technology and regression analysis are used for qualifying a chromatography system. In order to practice the present invention, certain steps must be performed. The initial step involves preparing the chromatography system to ensure that the samples, solvents, and the separation column are ready for analysis. After the chromatography system has been prepared, automated steps are performed to qualify the detector, the solvent delivery system, the sample manager, the gradient proportioning system, the column heater, and the delay volume of the chromatography system. Regression analysis is performed to compute performance statistics that demonstrate the accuracy, linearity, and precision of the chromatographic system and quantify its suitability for chromatographic analysis.

In an illustrative embodiment, the automated qualification systems application is built using the Millennium[32] vV3.20 Toolkit Option (Professional Edition, Waters Corporation) and Microsoft Visual Basic 6.0 (Enterprise Edition, Microsoft Corporation).

Advantages of the invention include the use of automation technology to provide a substantially faster way to qualify chromatography systems. Less time is required for qualification, thus the cost of qualification is lowered enabling more frequent qualifications. The method according to the invention minimizes contamination of the chromatography systems with solutions which are not suitable as mobile phases that could interfere with normal operation in subsequent analyses. The testing is based on "normal/intended" use of chromatograph and data system, which is consistent with the current FDA regulations and does not use procedures and materials substantially different from the primary application. Further, the operator, after initial procedures are performed, is allowed to utilize their time attending to other matters, as the invention requires no additional human intervention during the qualification process. The production of various reports in an electronic format allows off site review and the generation of varied format reports. Test results can be archived in an efficient electronic format.

BRIEF DESCRIPTION OF THE DRAWINGS

The foregoing and other features and advantages of the present invention will be more fully understood from the following detailed description of illustrative embodiments, taken in conjunction with the accompanying drawings in which.

DETAILED DESCRIPTION

Figure 1:
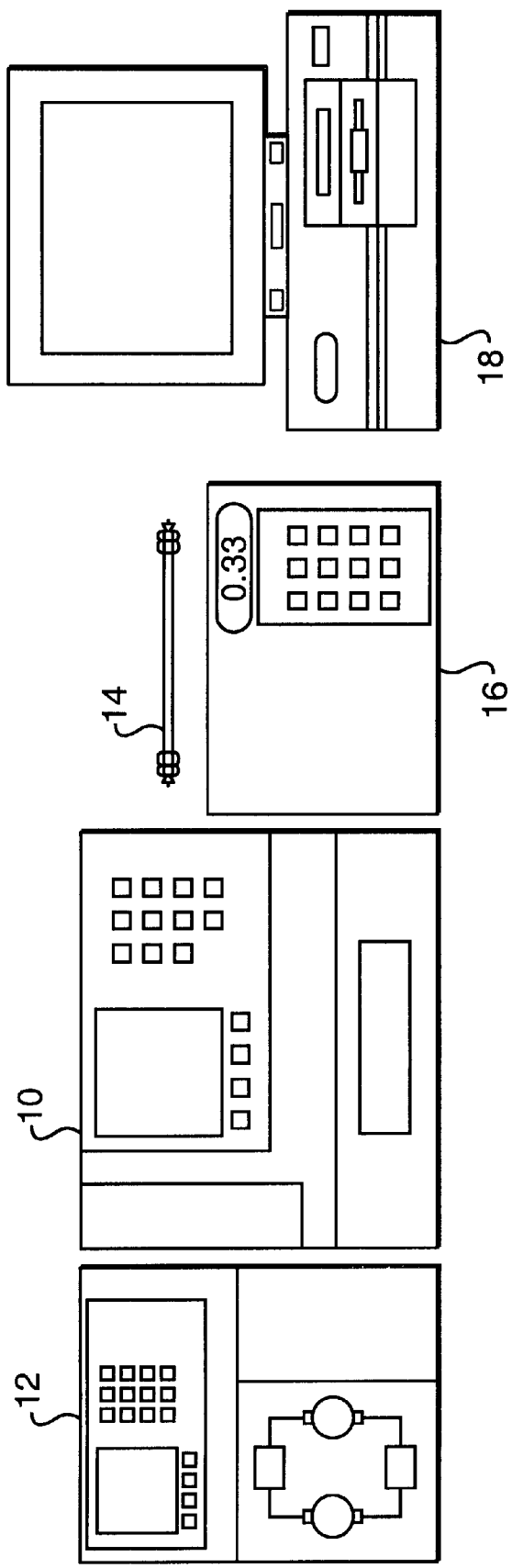
FIG. 1 shows a typical chromatography system.

As shown in FIG. 1, a conventional chromatography system typically includes a solvent delivery system 12, a sample manager 10, a column 14, a detector 16, and a Data System 18 The present invention provides a method of using automation technology for qualifying chromatography systems as required by the FDA.

Figure 2A:
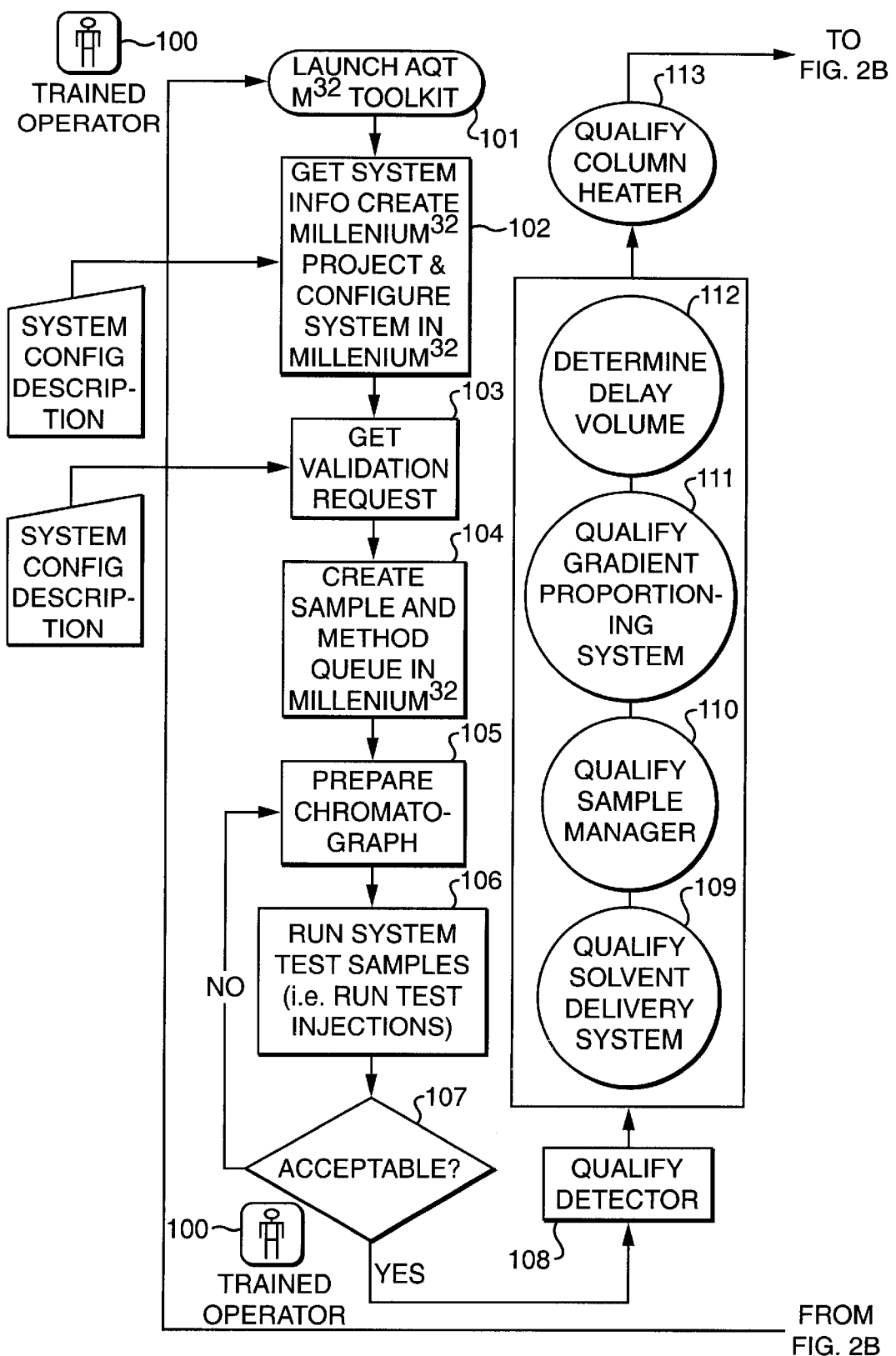
FIG. 2 shows a flow chart of the steps used to qualify a chromatography system according to the present invention.
Figure 2B:
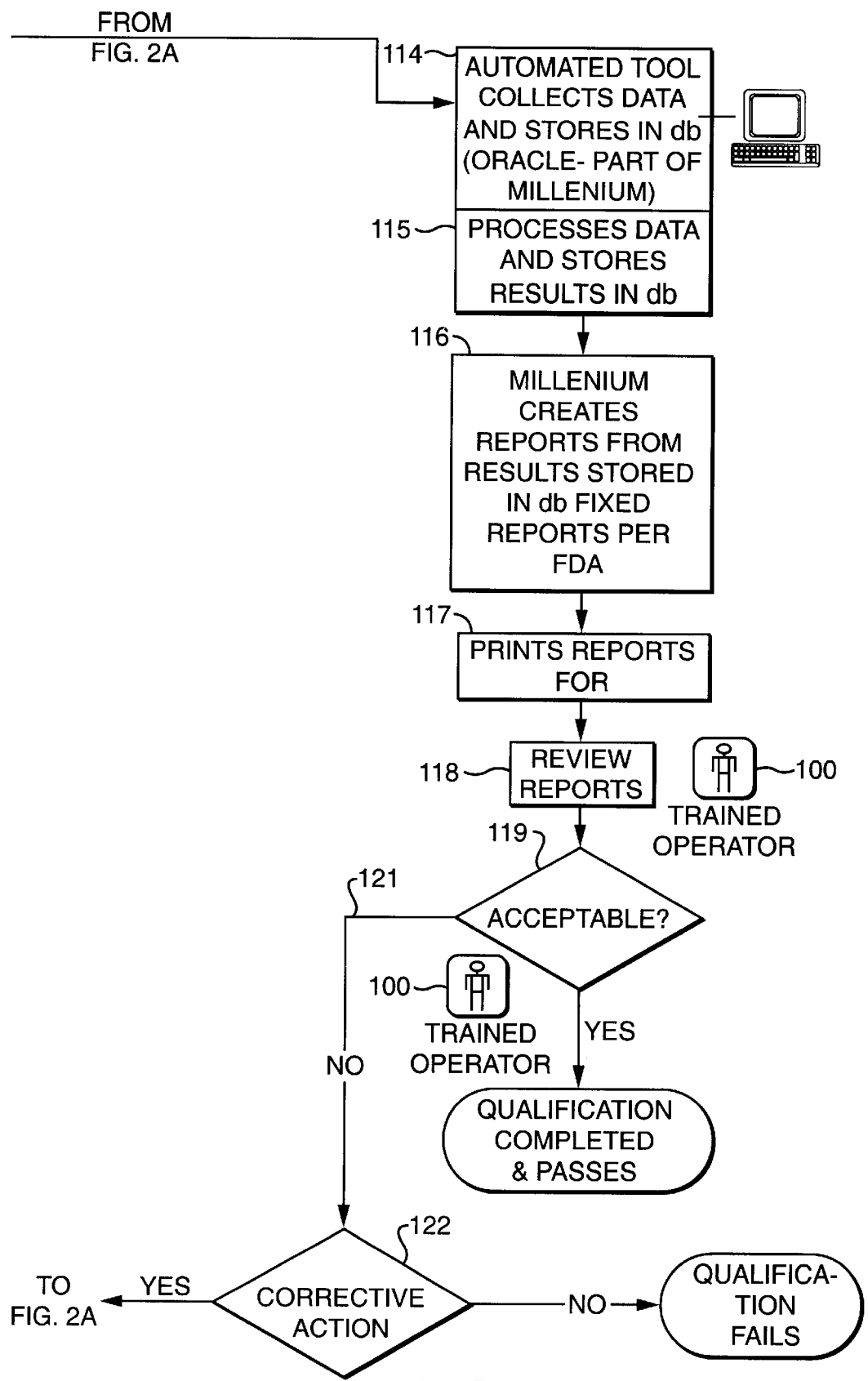

A flow chart as shown in FIG. 2 illustrates the steps of an illustrative embodiment for performing a qualification according to the invention. In the illustrative embodiment the automated method is initiated by launching 101 a Millennium$^{32}$ Toolkit. Upon the launch 101 of the Toolkit, the application retrieves the system information from an Oracle database 204 (FIG. 3) and creates a Millennium project and configures 102 the system in accordance with Millennium as is known in the art. The application is then configured 102 according to the project selected. The configuration 102 of the application incorporates the control of various components of the application. The selection of the project type and the acquisition server are completed within the configuration 102 of the system. The chromatographic system is identified and the specific features of that system are confirmed. The presence of a column heater and the type of detector that is to be used for qualification are selected. The selection of the type of flow cell contained within the chromatographic system and the different instrument modules contained within the system are identified during the configuration 102 step and confirmed. The system is then validated 103 based upon the configuration 102 step. Based upon the qualification method selected during the configuration step 102 the application creates a matrix 104 with a specific sample and method queue within the Millennium$^{32}$ application. The methods that are selected during the configuration step 102 are specific for the various qualification methods within the illustrative embodiment. The matrix determines the specific chemistries and mathematical algorithms employed within a specific chromatography column.

Once the configuration 102 of the system has been completed, the trained operator 100 of the chromatography system prepares 105 the chromatograph for the automated qualification of the chromatography system. The trained operator 100 during the preparation step 105 verifies that the samples required for the entire qualification procedure are in the proper location in the proper carousels. The preparation 105 entails setting up the solvent manager, placing standard samples in the sample manager, and equilibrating the chromatographic column to ensure that the system is well equilibrated and ready for analysis.

Once the preparation 105 of the chromatograph is completed, test injections 106 are run which verify that system preparation 105 is completed correctly. If the test injections 106 are within the specifications the trained operator 100 queues the running of the automated qualification process and the additional tests needed for qualification are then performed automatically without the need for trained operator 100 intervention. If the test injections 106 are not within specifications the preparation 105 of the chromatograph is repeated.

As illustrated in FIG. 2 it is critical that the qualification of Detector 108 is done first, since most of the remaining measurements are based on the accuracy and linearity of the detector. The qualification of a solvent delivery system 109, a sample manager 110, a gradient proportioning system 111, and the delay volume 112 are conducted in the illustrative embodiment in a sequence 120 shown in FIG. 2. This sequence 120 is not critical and in alternative embodiments the steps can be performed within a different sequence or performed substantially simultaneously. The qualification of the Column Heater 113 is optional since not all systems include this component. The Column Heater qualification 113 requires increasing the column temperature. It must therefore be done after the sequence 120 shown in FIG. 2. It is critical that the Column Heater qualification 113 be done after the sequence since chromatography systems usually have no active cooling mechanism.

Figure 3:
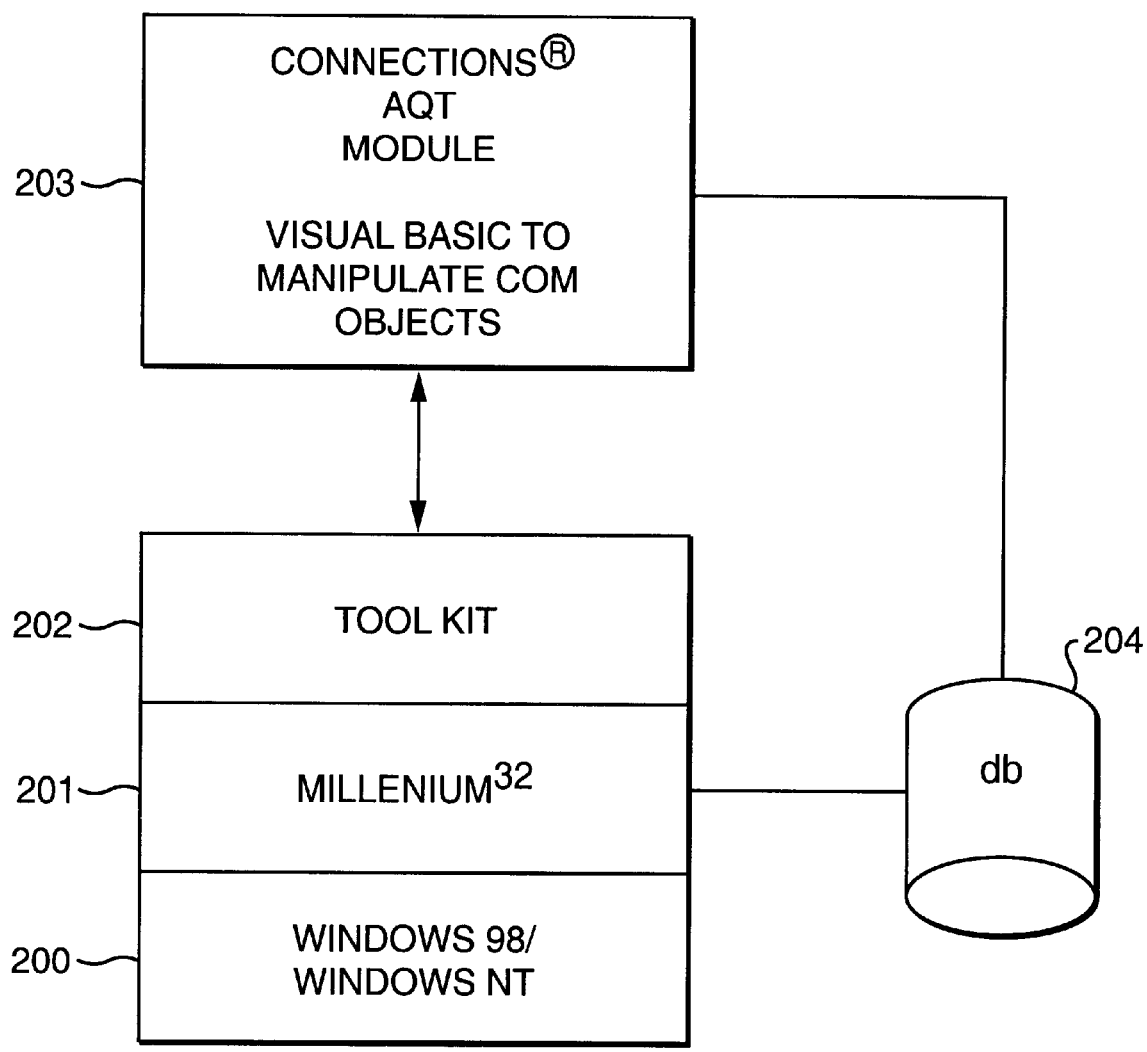
FIG. 3 shows an illustration of the software components utilized in the development of the application.

In conformance with the methods that are created in the sample and method queue 104, data is collected 114 that is generated by the automated qualification process and placed within an Oracle database 204 (FIG. 3). The collected data 114 is processed 115 and the results are stored within the database 204 (FIG. 3). The Millennium$^{32}$ 201 (FIG. 3) software then creates reports 116 in a format that is in conformance with regulatory requirements. A hard copy 117 of the reports 116 is printed for review 118 by the trained operator 100 of the chromatography system. The trained operator 100 confirms either the compliance 119 of the chromatography system or the failure 121 of the chromatography systems to perform within acceptable standards. Based on the generated reports 116 any deficiency within the system is identified and corrective action 122 is performed.

Referring to FIG. 3 the automation, analysis, and generation of the above qualification method is accomplished within the illustrative embodiment by utilizing an add-on application 203 to the Millennium³² software 201 (Waters Corporation). This add-on application 203 is built using the Millennium³² v.3.20 Toolkit Option 202 (Professional Edition, Waters Corporation) and Microsoft Visual Basic 6.0 (Enterprise Edition, Microsoft Corporation). The Millennium³² version 3.20 Toolkit 202 consists of a Toolkit Server, a Toolkit Extensions Server and the ActiveX Processing Control. Millenium Toolkit 202 is described in detail in Toolkit Programmer's Reference Guide, P/N 71500016005, Revision A available from Waters Corporation Milford, Mass., which is incorporated herein by reference. The Toolkit 202 is essentially an Applications Programming Interface (API) that defines the servers' objects and their methods and properties. Only pre-built objects available in Visual Basic 6.0 such as the form, the frame the command button, and the checkbox are used in the creation of the add-on 203 application. The add-on 203 application utilizes the Toolkit 202 and the underlying Millenium³² 201 application running on Windows 98/Windows NT 200.

The Millennium³² Toolkit 202 is based upon component integration technology commercially available in the software industry, the Microsoft Component Object Model ("COM"). The Toolkit Option 202 contains over 30 programmable COM objects that allow the use of development platforms such as Microsoft Visual Basic or Microsoft Office to create specialty applications that work interactively with the Millennium³² 201 software. The basic operation of the Millenium Toolkit 202 is in a wizard format. The resulting application 203 is compliant with the FDA's Electronic Records and Signatures Rule (21CFR Part 11), which is a requirement for any laboratory operation under Good Laboratory Practice ("GLP") or Good Manufacturing Practice ("GMP") because Millennium³² is compliant.

In order to record details such as IQ data a table is created in Millennium³² Oracle database. Criteria associated with qualification data are the main make up of the table. A sequence is also created so that each record in the table is given a unique ID. Each type of record is version controlled and new versions will be recorded when new work is carried out. The records are stored in the database table. In this illustrative embodiment there is no delete functionality available. If there are discrepancies with the current IQ record then the trained operator 100 can re-write the details and store a new record. Instead of calling external SQL scripts the application uses the Command objects of a Data Environment Designer connection object. The data source is accessed using ActiveX Data Objects (ADO) from an OLE® DB provider for Oracle.

ADO is designed as an easy-to-use application level interface to Microsoft's data access paradigm, OLE® DB. OLE® DB provides high-performance access to any data source, including relational and non-relational databases, email and file systems, text and graphics, custom business objects, and more. ADO is implemented within the illustrative embodiment for minimal network traffic in key Internet scenarios, and a minimal number of layers between the front-end and data source. The above methods provide a lightweight, high-performance interface. ADO is called using a familiar metaphor, the OLE® Automation interface.

OLE® DB is a low-level interface that introduces a "universal" data access paradigm. That is, OLE® DB is not restricted to ISAM, Jet or even relational data sources known in the art, but is capable of dealing with virtually any type of data regardless of its format or storage method. This versatility means that data in the illustrative embodiment can be accessed that resides in an Excel spreadsheet, text files, or even on a mail server such as Microsoft Exchange.

In the illustrative embodiment Visual Basic 6.0 is utilized to increase the flexibility of OLE® DB through ADO, programmer interface. Since OLE® DB is not designed to be accessed directly from Visual Basic due to its complex interfaces, ADO encapsulates and exposes virtually all of OLE® DB's functionality. Additionally, the Data Environment Designer provides an interactive, design time environment for creating programmatic run time data access. The property values are set for the Connection and the Command objects, write code to respond to ADO events, execute Commands, and create aggregates and hierarchies. The Data Environment objects are also placed onto forms or reports to create data-bound controls.

The Data Environment designer is used to create a Data Environment object. The Data Environment object includes Connection and Command objects, groupings, and aggregates. In designing the Data Environment the database is identified that contains the information for the run-time objective of creating a Data Report.

To access data using the Data Environment, a Connection object is created. Every Data Environment includes at least one Connection object. A Connection object represents a connection to a remote database that is used as a data source. Upon adding a Data Environment to the Visual Basic project, the Data Environment designer automatically includes a new connection, called Connection1. The configuration of the illustrative embodiment is such that the Data Environment opens the connection and obtains metadata from the connection, including database object names, table structures, and procedure parameters. The source for the data environment connection is defined using the data link properties dialog box. In the illustrative embodiment, the Microsoft OLE® DB provider for Oracle is the choice.

The Command objects in this application are based on both the database table object and Structured Query Language (SQL) queries. Use is made of the fact that pre formatted Commands to carry out SQL queries can be revised at run time so that the changed query variables will cause data retrieval to change.

The Microsoft Data Report designer is used in conjunction with the data source of the Data Environment designer, reports are created from the database qualification table for IQ. In addition to creating printable reports, one can also export the report to HTML or text files. As previously indicated query criteria change so to does the output of the report as the controls on the report are bound to the changed Command.

The sample set methods to be chosen depends on the configuration 102 indicated by the trained operator 100 of the automated test system. The value properties are examined for the various qualification and text Checkboxes and the status indicated on the Configuration Frame. Whether a system is tested for Operational & Performance Qualification or full System Qualification there are different sample set methods to be used. The three variables "Detector Type", "Temperature Control" and "Cell Type" influence the selection. Hence a three dimensional sample set matrix/array with the above coordinates and containing various suffixes is provided within the software. When the suffixes are concatenated with the chosen tests to be performed the result is a run sequence that can be passed to the instrument server. As shown in FIG. 2, a series of test injections 106 is always used as part of the run as a precursor to successful qualification. Queuing the sample sets involves the initiation of a Toolkit Instrument object and using the run method with the names of the sample set methods. A timer cycle is used to enable the monitoring of Toolkit Instrument connection status. Each and every time a proposed run is to be queued the revision number for qualification attempts is incremented in the database table. The increment is also tied to the sample set name that appears in "Run Samples".

Figure 3A:
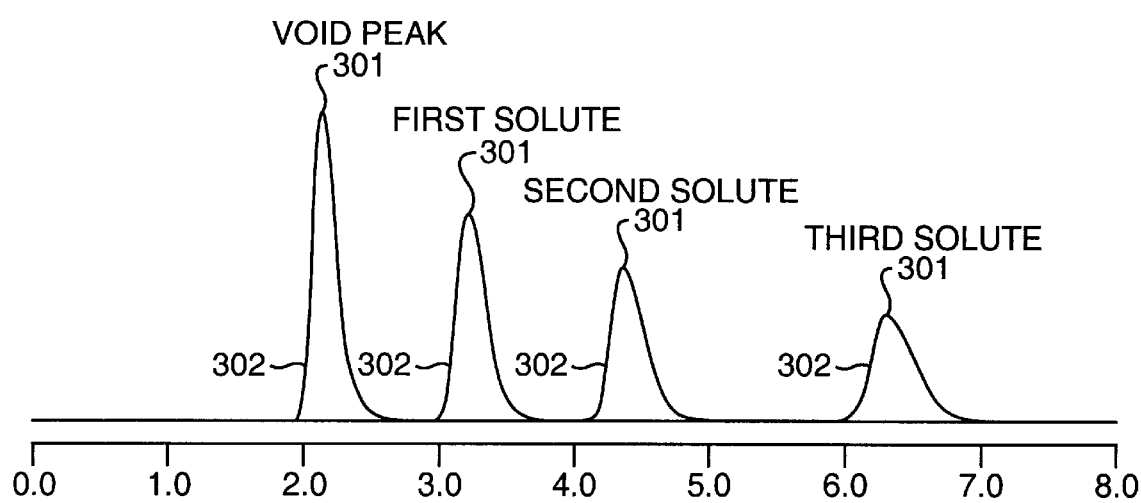
FIG. 3a shows a typical chromatogram

The following chemistries and mathematical theories of the illustrative embodiment allow the above software to integrate the installation, operational and performance qualifications procedures into an automated system process by developing standards that are linear and therefore amenable to automated analysis. The quantitative analysis of a standard chromatogram as shown in FIG. 3a requires the association of a peak area (or height) with the mass or concentration of the analyte injected via an appropriate calibration curve constructed from the injections of standards. The principal parameters associated with a chromatogram are the retention times 301 and peak areas 302. The general metrics of instrumental analysis for the reported responses (retention times 301 and peak areas 302) are the basis of qualification for both manual and automated systems. The precision, accuracy, and linearity of retention times 301 and peak areas 302 are dependant upon factors discussed below. The detector performance parameters that are measured in the present invention during the qualification of the detector which most directly affect the chromatograms are linear dynamic range and wavelength accuracy. Other detector performance parameters such as detector dispersion, noise, and drift are highly method dependent. Therefore, it is not useful to produce automation for those factors that are not universal in their impact.

Figure 4:
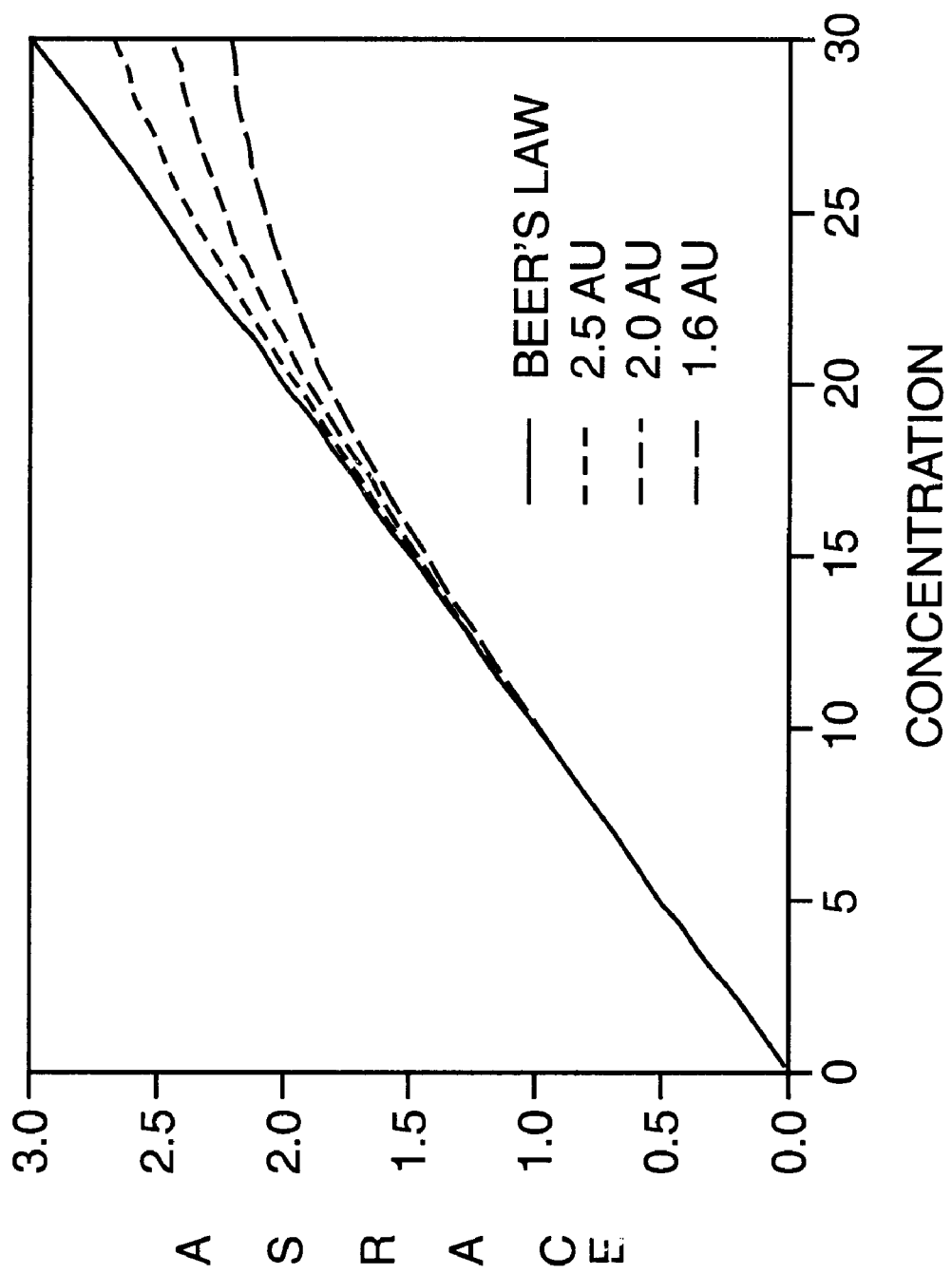
FIG. 4 shows an illustration of the response curves for detectors demonstrating various linear dynamic range values.

Referring to FIG. 4, an illustration of the response curves for detectors demonstrates various linear dynamic range values. The value associated with each calibration curve is the absorbance at which the observed value is 95% of the value predicted by Beer's Law in accordance with an older ASTM protocol. The procedure calls for the drawing of the curved line which fits the data and the extrapolation of the initial slope. This is followed by an estimation of the 5% negative deviation point. The procedure is highly subjective and not adaptable for an automated test system. An alternate approach utilized in the qualification of the detector in the illustrative embodiment, that is amenable to automation, also relies on Beer's Law.

$$A = \epsilon * b * C$$

If the measured absorbance is divided by concentration, the apparent sensitivity is calculated.

$$S = A/C = \epsilon * b = \text{constant}$$

The apparent sensitivity, S, is not constant over the dynamic range of the instrument, but the magnitude of the relative standard deviation (%RSD) of the sensitivity is a good measure of its degree of variation. If sensitivities are measured at values of absorbance which fall on both the linear and curved portions of the calibration curve, this RSD of the sensitivity becomes a good measure of linear dynamic range.

An example of such a calculation is shown hereinafter in Table 1.

TABLE 1

Linear Dynamic Range Calculation Based on Sensitivity

| Concentration | 2.5 AU | 2.0 AU | 1.6 AU | S_2.5 AU | S_2.0 AU | S_1.6 AU |
|---|---|---|---|---|---|---|
| 5  | 0.499 | 0.498 | 0.495 | 0.0998 | 0.0995 | 0.0990 |
| 10 | 0.996 | 0.990 | 0.980 | 0.0996 | 0.0990 | 0.0980 |
| 15 | 1.486 | 1.467 | 1.436 | 0.0990 | 0.0978 | 0.0957 |
| 20 | 1.955 | 1.901 | 1.820 | 0.0978 | 0.0950 | 0.0910 |
| 25 | 2.371 | 2.241 |       | 0.0948 | 0.0896 |        |
| 30 | 2.678 |       |       | 0.0893 |        |        |
|    |       |       | % RSD | 4.21   | 4.22   | 3.72   |
|    |       |       | Max AU| 2.678  | 2.241  | 1.820  |

The calculation is illustrated as such for the detector labeled 2.5 AU and the slope of the calibration curve has a relative standard deviation of only 4.21% for absorbances ≦2.678. The detector labeled 1.6 AU has a relative standard deviation of 3.72% for absorbance ≦1.82.

This approach does not require non-linear curve fitting like prior manual methods illustrated in FIG. 4 and generates numerically simple results, that are used in the illustrative embodiment for the qualification of the detector 108 that is adaptable for the automated system of the present invention described herein before. The selection of specific target absorbance values and setting of control values for the %RSD observed for a specific detector model can be done in a straightforward manner, if non-linearity is modeled as stray light.

$$A_{meas} = \log_{10}\{(1 + \%s/100)/(10^{-A} + \% s/100)\}$$

where $A_{meas}$=the measured absorbance, A=true absorbance in absence of stray light, and %s=the stray light expressed as a percent.

By setting $A_{meas}$=0.95 A, the apparent stray light for a given value of linear dynamic range (expressed as absorbance at which there is a 5% deviation from linearity) can be calculated. Thus, the control value for %RSD of the apparent sensitivity can be directly correlated to the design specification for a specific detector.

The choice of a probe compound in the present invention is based on ensuring that the boundary conditions for Beer's Law are met. In the illustrative embodiment the above conditions are: spectral bandpass is small relative to peak width, dilute solution, constant refractive index, and simple chemical equilibrium. In this illustrative embodiment, caffeine dissolved in water:methanol mixture and measured at 272 nm meets all of the criteria and is stable and available in high purity.

The linear dynamic range of a detector is best measured at $\lambda_{max}$. This ensures that wavelength accuracy errors will not contribute to the measurement of linear dynamic range and that the spectral bandpass (slit width) of the detector will have minimum impact on the measurement. This is consistent with good spectroscopic practice. To determine the linear dynamic range of a detector, a series of samples which generate chromatographic peaks with heights ranging from 0.1 to 2.2 AU is injected into the chromatography system. The probe compound used for wavelength accuracy is also used for the measurement of linear dynamic range. This reduces the number of different samples and solvents required for qualification and ensures that the linear dynamic range is measured at $\lambda_{max}$.

In order to verify the wavelength accuracy of the detector during the qualification of the detector 108 of the present invention, a probe compound must be selected. Suitable probe compounds must not react with the column or any of the solvents. It also should have well defined characteristics that can be traced back to known (well characterized) standards. Most importantly, the UV spectrum of the probe compound must have at least two well resolved absorbance peaks which should be in the primary wavelength range of absorbance detectors (200–400 nm).

Table 2 shown below summarizes several probe compounds which are helpful in measuring wavelength accuracy in HPLC detectors.

The OQ of fluorescence detectors, in the automated process of the illustrative embodiment present invention, is accomplished by the principles set forth below. Fluorescence detectors operate by irradiating the sample with light at an excitation wavelength ($\lambda_{ex}$) and measuring the intensity of the light emitted at the emission wavelength ($\lambda_{em}$). The relationship between concentration and the observed intensity of emission is given by Equation 1.

$$\text{Fluorescence} = F = f(\theta) * g(\lambda_{em}) * \phi_f * P_o(\lambda_{ex}) * (1 - \exp\{\epsilon b C\}) \quad \text{Equation 1:}$$

Where $f(\theta)$ is the geometric collection efficiency of the detector, $g(\lambda_{em})$ is the photomultiplier's response at the emission wavelength, $\phi_f$ is the quantum efficiency of the analyte, $P_o(\lambda_{ex})$ is the radiant power of the source at the excitation wavelength, $\epsilon$ is the molar absorbtivity, b is the path length, and C is the concentration of the analyte.

Equation 1 can be simplified by combining constants and expanding the exponential term in a Taylor series to give Equation 2.

$$\text{Fluorescence} = F \cong \text{constant} * P_o(\lambda_{ex}) * C \quad \text{Equation 2:}$$

This equation is correct only for small values of absorbance (<0.01) where the second order and higher terms of the Taylor series can be ignored. Examination of Equations

TABLE 2

Wavelength Accuracy Probe Compounds

| Name | Solvent | Wavelength(s) | Note(s) |
|---|---|---|---|
| Erbium (III) Perchlorate | Water | 255, 379, and 523 nm (all peaks are highly symmetric) | NIST and ASTM traceable; multiple wavelengths over wide range; simple chemistry. |
| Caffeine | Water:methanol | 205 and 272 nm | Two points covering primary wavelength range; easily automated. |
| Uracil | Methanol | 257 nm | Highly symmetric absorbance peak; compatible with detectors having larger spectral bandpass. |
| Anthracene | Water: Acetonitrile | 252 nm | Highly asymmetric peak at 252 nm; acceptable choice for detectors with small (≦5 nm) spectral bandpass |
| Holmium oxide | Perchloric acid (10% in water) | Multiple asymmetric peaks | NIST traceable; best for detectors with cuvette accessory; requires very narrow (≦2 nm) bandpass |

The first two compounds are the favored choices for wavelength accuracy measurements. Uracil is suitable for wavelength accuracy measurements for older detectors which have larger spectral bandpass values.

One suitable probe compound is a solution of caffeine dissolved in methanol and water. A UV spectrum of the caffeine, methanol, and water solution has principal absorbance peaks at 205 nm and 272 nm. The observed wavelength of maximum absorbance (lambda max, $\lambda_{max}$) must match the reference values within the detector specifications, typically ±1.5 to 2 nm.

In the OQ of photodiode array detectors (PDA), which acquire an absorbance spectrum rather than the primary single wavelength data that conventional absorbance detectors acquire, the OQ of the detector remains the same. The wavelength accuracy and linear dynamic range are the variables that either a manual qualification or as in the present invention an automated qualification need to access.

Measurement of the linear dynamic range of a PDA detector ensures that both stray light and resolution are unchanged from the design parameters of the detector.

1 and 2 indicate that the following parameters will strongly influence the observed fluorescence signal. These parameters are as follows: excitation wavelength, emission wavelength, source intensity, the excitation wavelength, response characteristics of the photomultiplier tube, concentration of the analyte, and the quantum efficiency of the analyte.

The first four factors are directly coupled to the detector while the last two factors are strongly assay dependent. The suitability of a fluorescence detector to perform chromatographic analysis can be determined by confirming wavelength accuracy for both the excitation and emission monochromaters and confirming that the signal to noise of a stable luminescence process meets an acceptance criteria. Because the absolute magnitude of the fluorescence signal is directly proportional to the source intensity which will vary as the lamp ages, it is not possible to benchmark performance to the peak height under specific gain conditions. A more measurable approach for the determination of the condition of the detector is to measure the signal to noise ratio for a well-known luminescence signal.

The Raman shift of water provides a convenient test probe for fluorescence detectors. When water is irradiated with light, most water molecules scatter the light elastically, i.e., with no transfer of energy. A small fraction of the water molecules absorb sufficient energy and re-emit the photon at a lower frequency. If the excitation light is at 350 nm, the Raman scattering is observed at 397 nm. The signal to noise ratio of the emission peak at 397 nm and its location at 397 nm confirm the suitability of the detector with respect to response and wavelength accuracy. The observed signal to noise ratio for the Raman band of water will reflect the source intensity, the purity of the water used for the measurements (HPLC grade water is appropriate), and the signal processing (including filtering, spectral bandpass of both monochrometers, and the illuminated volume of the flow cell). The Raman signal to noise ratio should meet or exceed the manufacturers' specification. If either the excitation or emission monochrometer's wavelength accuracy can be independently verified, the relationship between the observed $\lambda_{max}$ of the Raman band (397 nm with 350 nm excitation) can be used to verify the remaining monochrometer. If the flow cell is removed and the photomultiplier gain is kept small, the presence of Hg emission lines in the light from fluorescent room lights can be used to verify the wavelength accuracy of the emission monochrometer.

Verification of linear dynamic range for a fluorescence detector is not required because Equation 1 is inherently non-linear and behaves linearly only under specific conditions. Two additional phenomena—the so-called "inner filter" effect and self-absorbtion—add additional exponential terms to Equation 1. The inner filter effect occurs when the sample (or its solvent) absorbs a portion of the excitation energy in a portion of the flow cell which is not imaged onto the emission monochrometer. The result is that the radiant energy is decreased without a concurrent increase in the measured emission intensity. If the absorbance spectrum overlaps the emission spectrum, some of the photons emitted by the analyte molecules will not be observed. The magnitude of both of these effects is dependent upon the analyte concentration. Consequently, the linear dynamic range of a specific assay will be highly dependent upon the specific concentration range and solution conditions and is verified as part of system suitability and calibration for this particular assay within the automated qualification system.

Figure 5:
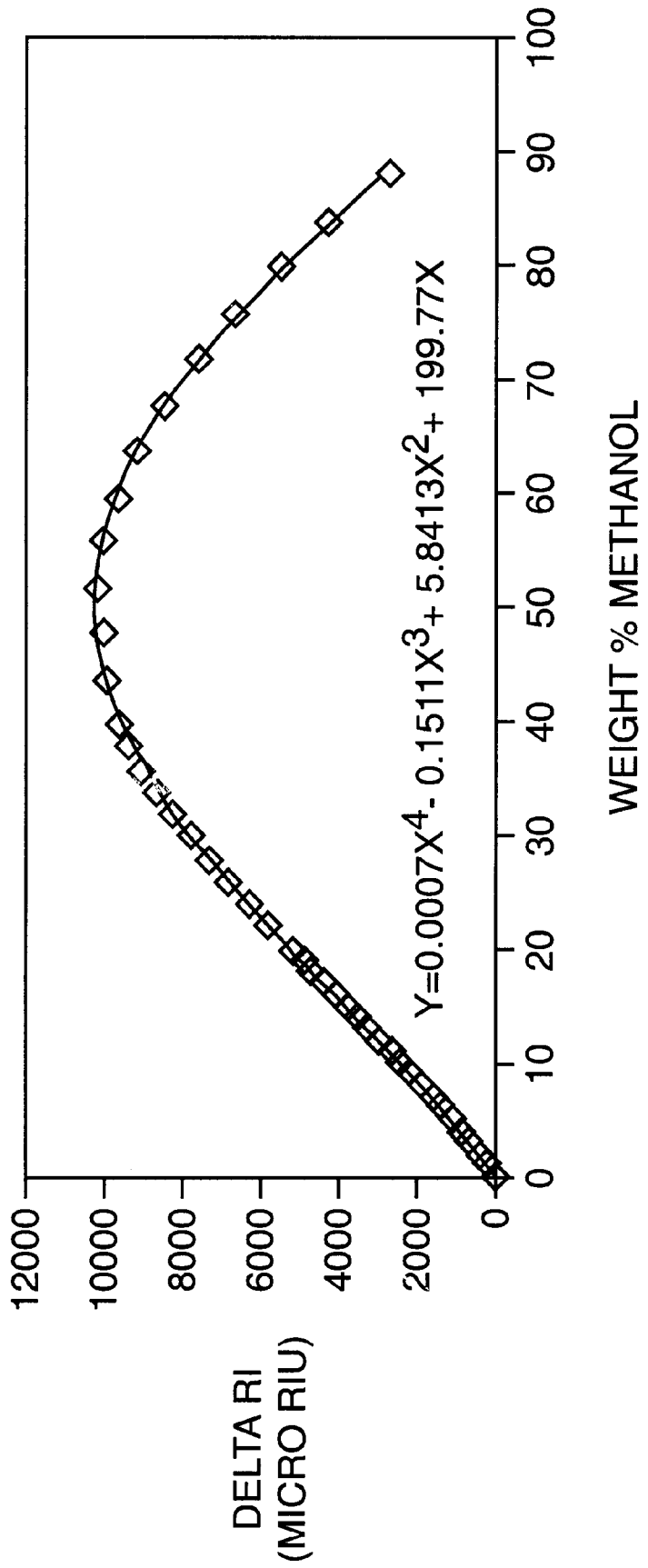
FIG. 5 illustrates that the change in refractive index with concentration is not necessarily a linear phenomenon.
Figure 6:
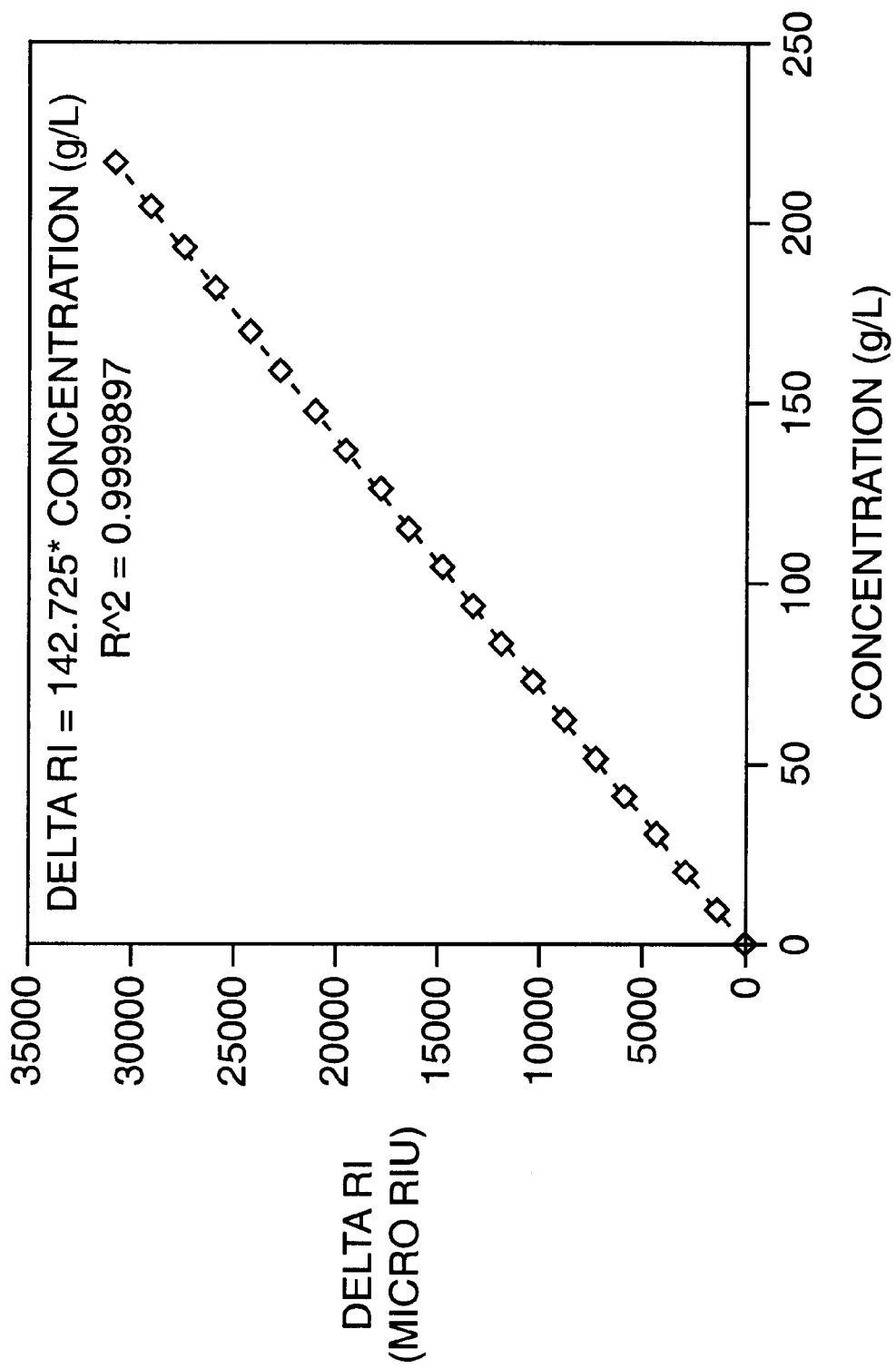
FIG. 6 illustrates that the change in refractive index of sucrose water mixtures is linear over a wide range of compositions.

Refractive index detectors are bulk property detectors, i.e., they respond to differences in the refractive index of the mobile phase when the analyte is eluted from the column. Consequently, it is necessary to stabilize the refractive index of the mobile phase in order to achieve good signal to noise ratios when small analyte peaks are eluted. Testing of the refractive index detector is, of necessity, a system level test and cannot be performed at a unit level. The change in refractive index with concentration is not necessarily a linear phenomenon as illustrated by the water methanol data shown in FIG. 5. Consequently, it is necessary within an automated system, to exercise care in the selection of both the analyte used to probe the linearity of detector response as well as the solvent used as the mobile phase. Ideally, a small molecule which is readily available in high purity and has a wide range of concentrations over which the change in refractive index is linear should be used for PQ testing of RI based HPLC systems. Representative data for the variation of refractive index of sucrose water solutions is shown in FIG. 6.

The protocols used to qualify systems with absorbance detectors exploit the high sensitivity of absorbance detection as well as its linear dynamic range. The mass loading of the columns in typical reverse phase separations is typically a small fraction of the column's linear dynamic range. Consequently, by increasing the concentrations of the reverse phase solutes by a factor of 100× the chromatograms obtained with differential RI (DRI) detection will possess appropriate signal to noise ratios.

The detector linearity, injector linearity, injector area precision, retention time precision and flow rate accuracy with DRI is performed using pre-mixed mobile phase. The pre-mixed mobile phase allows the stable baselines required for unambiguous integration.

The performance qualification of a chromatograph which uses an absorbance detector is an assessment of baseline performance which the majority of chromatographic analyses will require. Because absorbance detectors have a wide linear dynamic range, the system performance parameters to be determined are isocratic retention time precision, peak area precision, and system linearity. A simple reverse phase separation (C18 column with methanol:water mobile phase) of stable analytes which cover a range of moderate values of k' is utilized in the present invention. A mixture of uracil and caffeine is used to generate chromatograms with a void marker (uracil) and a well-resolved retained peak suitable for quantitation. The mobile phase can be pre-mixed or mixed on-line if a gradient system is used. For gradient systems, on-line mixing should be used. Table 4 lists the appropriate control values for a general HPLC system.

TABLE 4

| | Control Values | | | |
|---|---|---|---|---|
| Peak | Retention Time RSD(%) | Area Precision RSD(%) | Height Precision RSD(%) | Linearity ($R^2$) |
| Uracil | 1.5 | 1.5 | 1.5 | N/A |
| Caffeine | 1.0 | 1.0 | 1.0 | >0.999 |

These values represent the maximum %RSD values that an analytical HPLC should generate on a simple isocratic separation.

The performance qualification of a fluorescence detector in the present invention is accomplished according to the following method.

Because fluorescence detectors do not have a wide linear dynamic range, the system performance parameters to be determined are isocratic retention time precision and peak area precision. A simple reverse phase separation (C18 column with acetonitrile:water mobile phase) of a stable analytes with a moderate k' is used. Anthracene is a native fluorophore which is readily separated on a C18 reversed phase column and is not strongly sensitive to oxygen quenching or dimer formation. The mobile phase can be pre-mixed or mixed on-line in a gradient system. As shown in Table 5 below the appropriate control values for a general HPLC system.

TABLE 5

Control Values.

| Peak | Retention Time RSD(%) | Area Precision RSD(%) | Height Precision RSD(%) |
|---|---|---|---|
| Anthracene | 1.0 | 1.0 | 1.0 |

These values represent the maximum % RSD values that an analytical HPLC should generate on a simple isocratic separation of anthracene using a fluorescence detector.

The performance qualification of refractive index detector within a chromatography system is automated by utilizing the principles set forth below using premixed mobile phases.

Measurement of flow rate accuracy and injection volume accuracy in the manual qualification of systems is generally based on measuring the time required to fill a volumetric flask (flow rate accuracy) or by weighing the mass removed from the sample vial (injection accuracy). Both techniques are manual and, it is desirable, in the illustrative embodiment to conduct an analysis that is subject to automation and less prone to human error.

The void volume of a chromatographic column is that portion of the column's nominal volume which is occupied by mobile phase, it includes the inter-particle and intra-particle volume. It is usually measured by adding an unretained small molecule, such as acetone, uracil, sodium nitrate, etc., to the sample mixture and measuring the product of the flow rate and apparent "retention time." Equation 3 relates the void volume to column parameters and flow rate.

$$V_o = \pi * d_c^2 * \epsilon * L/4 = t_o * V_f \quad \text{Equation 3:}$$

Where $d_c$=column diameter (cm), $\epsilon$=column porosity, L=column length (cm), $t_o$="retention time" for unretained component (min.), and $V_f$=volumetric flow rate (mL/min.)

Equation 3 can be re-arranged to give the following . . .

$$(1/t_o) = (1/V_o) * V_f = 1/V_o * (V_f + \text{error}) \quad \text{Equation 4:}$$

Consequently, a plot of the quantity $1/t_o$ vs. $V_f$ will be linear. If it is regressed against a linear equation of the form, $Y = A_o + A_1 * X$, and the X-intercept is computed. It will have the form.

$$X\text{-intercept} = -A_o/A = \text{flow rate error} \quad \text{Equation 5:}$$

Figure 7:
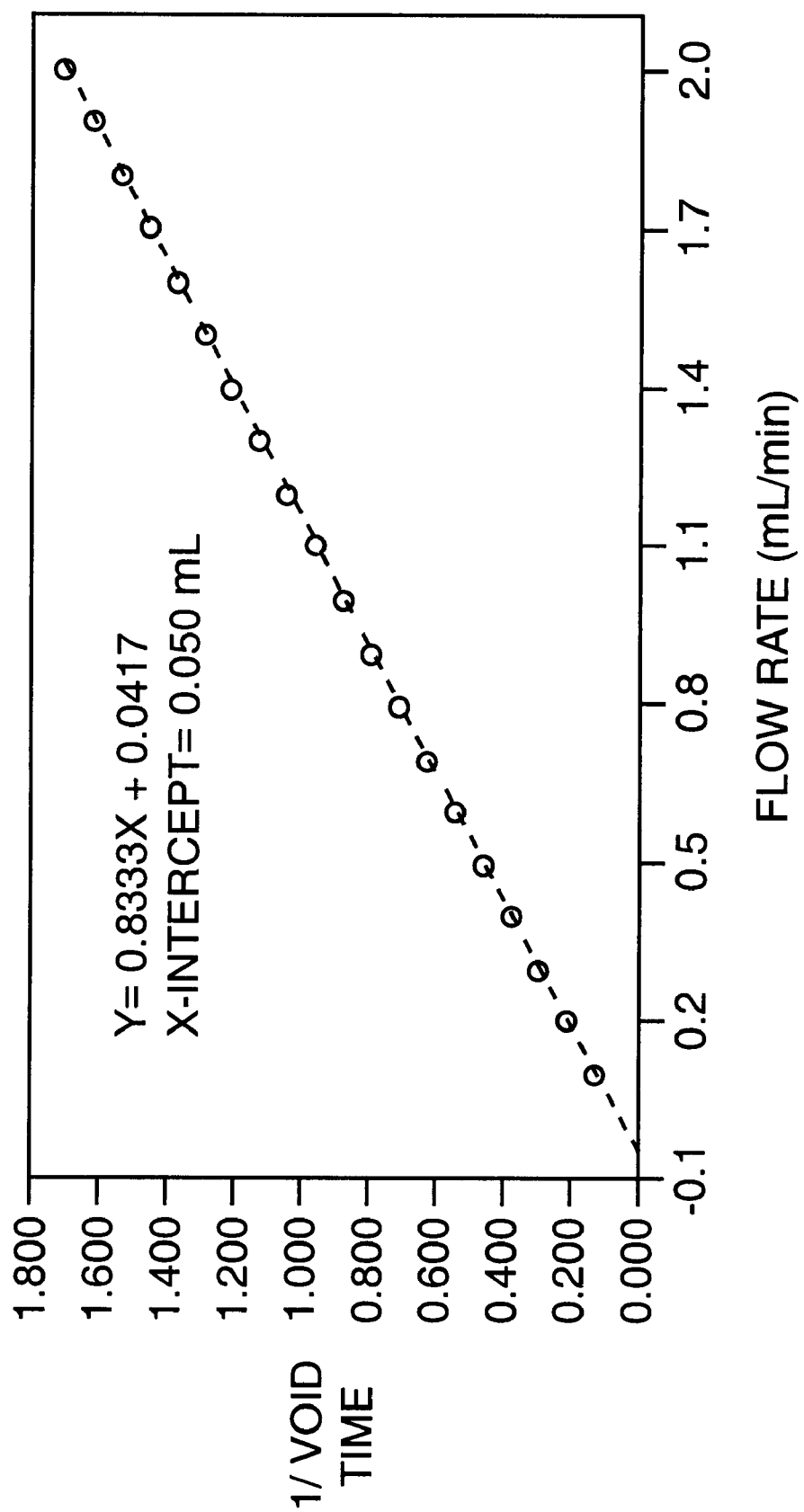
FIG. 7 illustrates a calculation relating the void volume to flow rate.

Referring to FIG. 7, Equation 5 is illustrated. The calculation has the advantage of computing a volumetric flow rate error term which includes contributions over the working range of the solvent delivery system and does not include contributions from the compositional errors of the pump because the peak is unretained.

To determine the linearity of the solvent delivery system 109, in the illustrative embodiment an appropriate sample of a non-retained compound (such as uracil or sodium nitrate) is eluted at several flow rates which span the active flow rate range. The unretained component is eluted at the void volume of the column. The peak area is related to the injection volume by equation set forth below:

$$\text{Area} = \text{constant} * \text{amount} = \text{constant} * V_{inj} * \text{concentration}$$

When a series of injections are made in which the $V_{inj}$ is varied and the sample concentration is held constant, the equation becomes:

$$\text{Area} = \text{constant} * (V_{inj} + \epsilon) = \text{constant} * V_{inj} + \text{constant} * \epsilon$$

Where $\epsilon$ is the volumetric error. Once again, if a plot of peak area is regressed vs. $V_{inj}$ the X-intercept is given by.

$$X\text{-intercept} = -\text{constant} * \epsilon / \text{constant} = -\epsilon$$

Figure 8:
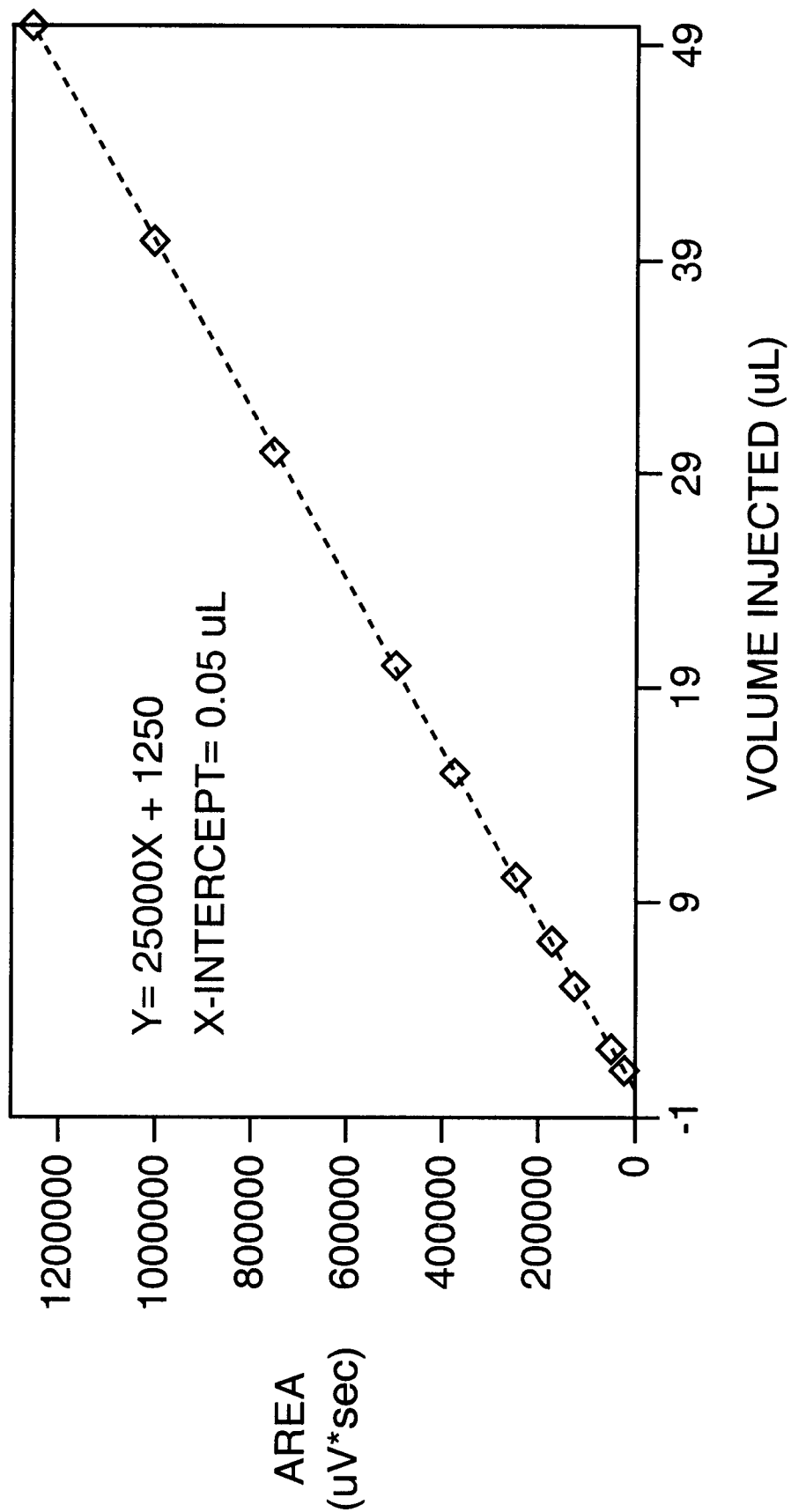
FIG. 8 illustrates injection volume accuracy.

FIG. 8 illustrates the above approach

The x-intercept is an estimate of the volumetric error of the quantity delivered and includes contributions over the full dynamic range of the instrument and estimates the systematic error in the quantity delivered to the column by the sample manager 110. This makes the approach appropriate to sample managers in which the sample is contained within the sample needle as well as those which transfer the sample to a sample loop.

In both the measurement of flow rate accuracy and injection volume accuracy, the values of the x-intercepts establish an error budget which can then be applied to the assay requirements. For example, the 0.050 mL/min. error is a 5% error at 1.0 mL/min, but is only 2% at 2 mL/min. The 0.050 μL error contributes a 2 parts per thousand error at 25 μL and 1% at 5 μL. This error budget should then be a part of establishing the system suitability criteria for a specific assay.

The qualification of the gradient proportioning system 111 is the measurement of the compositional accuracy based on shifts in retention time with small changes in composition; the system noise will be greater, but retention times are not strongly impacted by baseline noise if the signal to noise ratio is large. The compositional accuracy measures the degree to which the solvent management system can generate a specific solvent mixture. To determine the compositional accuracy, inject the same volumes of samples while using different combinations of reservoirs in the chromatography system. The relative standard deviation (% RSD) of the retention times is measured and those of caffeine should be fairly consistent. The qualification standard requires the relative standard deviation to be less than or equal to 2%.

The qualification of the delay volume 112 of the solvent management system is the volume of mobile phase that separates the gradient forming device from the column inlet. Ideally, the delay volume should be scaled to the void volume of the chromatographic column to ensure method transferability and efficiency. In prior manual qualification systems, the delay volume of a gradient solvent delivery system was measured by the volume required for a step change in mobile phase composition using a suitable marker compound (such as acetone or propyl paraben) to arrive at the inlet connection of the column. The column needed to be removed in such measurements. Both threshold-based and first derivative-based calculations have been used to determine the arrival time.

The delay volume of a gradient chromatography system is the volume contained in the solvent delivery system from the point at which the gradient is formed (the gradient proportioning valve in a low pressure gradient system) or from the first mixing "tee" where the solvents are combined (high pressure gradient system) to the column's inlet. Its significance arises from the need to qualify the gradient proportioning system 111 to ensure that that the delay volume is delivered to the column before the gradient change in mobile phase composition begins. It is a temporal offset in the gradient chromatogram. If all of the components of the sample are strongly retained in the initial conditions of the gradient, it is simply overhead that increases the separation time and the time required to re-equilibrate the column prior to the next injection. If sample components are not strongly retained at the initial conditions, the separation will contain peaks which are eluted under isocratic, gradient and mixed chromatographic modes. The relationship between k' and peak migration volume is given by:

Fraction of Column Volume Traveled=$V_R/\{V_o(1+k')\}$

Figure 9:
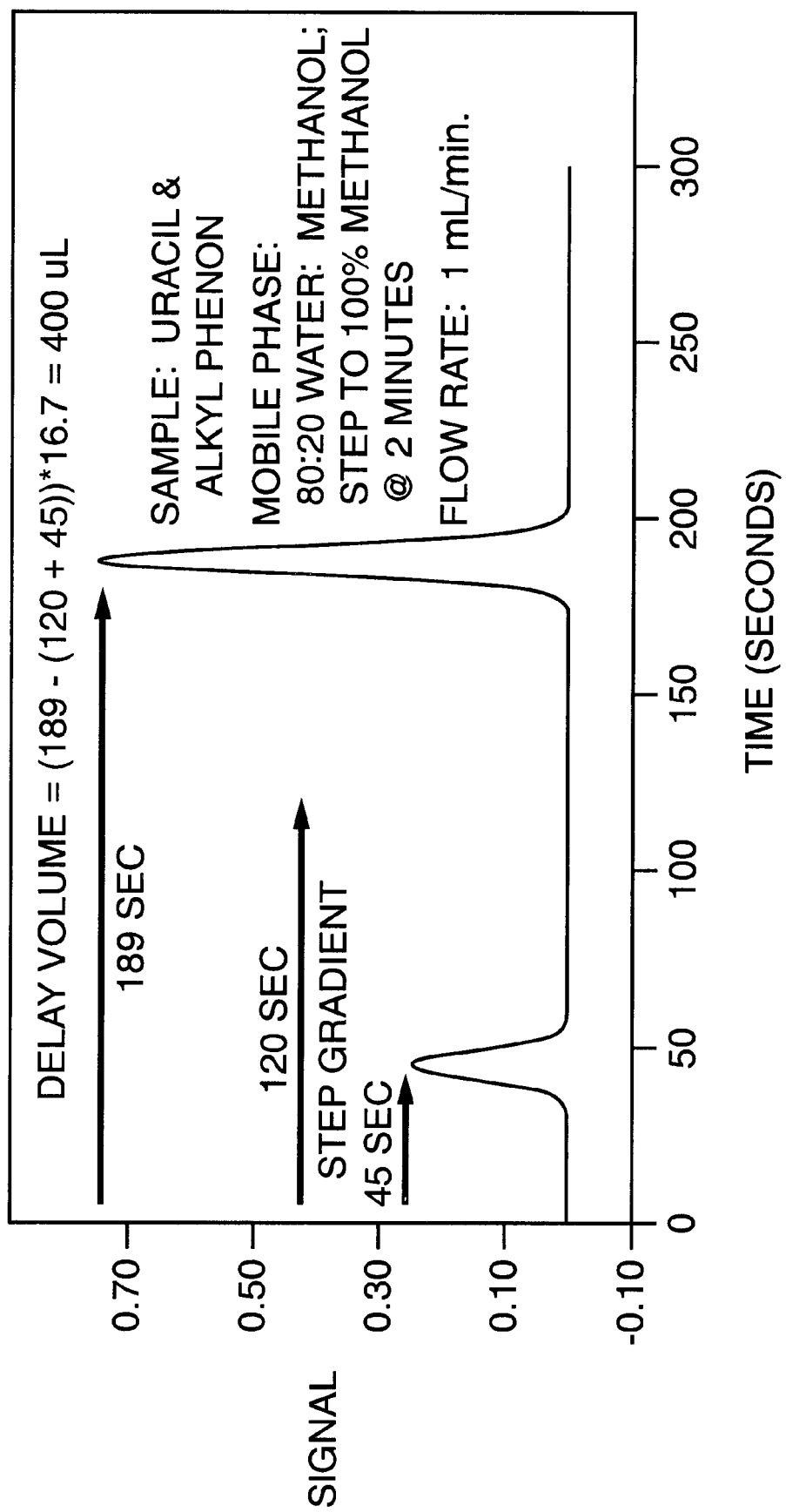
FIG. 9 illustrates the delay volume as well as the column void volume and the volume of mobile phase.

When $V_R$ is small, the fraction of the column that a strongly retained peak travels is very small and the solute is said to be "focused" at the inlet of the column. When k'=0, the unretained solute sees the delay volume from the injector to the column inlet, which should be minimized to reduce sample dispersion. If the mobile phase is stepped from the initial conditions to 100% organic modifier, the "focused" solute now becomes unretained and its migration volume includes the delay volume as well as the column void volume and the volume of mobile phase pumped at the initial conditions. Referring to FIG. 9 the above principle is illustrated.

In this illustrative embodiment FIG. 9, a mixture of an unretained and strongly retained compounds (such as uracil and octanophenone) are injected and the mobile phase composition is changed in a single step from the initial conditions to 100% organic modifier. The unretained compound will have a retention volume equal to the void volume of the column plus the tubing which connects the column to the injector and detector. The strongly retained compound will initially be focused at the column inlet and subsequently eluted as an unretained component after the step to 100% organic modifier. The retention volume of the strongly retained compound will be the sum of the delay volume, the volume of the connecting tubing, the void volume of the column, and the volume of solvent pumped at the initial composition. By subtracting the void volume (first peak) and the volume at initial conditions from the retention volume of the strongly retained solute and correcting for the volume of solvent pumped at the initial composition, the system delay volume is measured.

The qualification of the column heater 113 is essential in those systems that contain column heaters. The qualification of a column heater 113 is important in order to insure that the column heater can consistently provide a set temperature because retention times and mobile phase viscosity are both strongly dependent upon temperature. The performance of column heaters in a manual qualification system is determined by placing calibrated thermocouples or thermistors at, or near, the control point of the column heater and measuring the difference between the set temperature and the observed temperature. This approach requires the use of external meters to read the output of the thermocouple and is highly subjective because it depends upon the accurate location of the thermocouple at the control point of the column heater. Additionally, while this approach confirms that the column heater is controlling the set point, it does not measure the effectiveness of the column heater at actually heating the column. The approach set forth below has the advantage of requiring no additional devices, no manual data entry, and it is not dependent upon the location of the temperature probe for its accuracy. When the column heater is qualified 113, in the illustrative embodiment, all qualification steps will be performed at a temperature which is about 10° C. (degrees Celsius) greater than ambient laboratory temperature. The average retention time measured for the injections used for the measurement of the sample manager's precision are a good estimate of the retention time at this base temperature. The column heater is subsequently set to a temperature which is 20° C. greater than ambient. After the column is equilibrated at this new higher temperature a set of injections are made using the same sample and conditions for the determination of sample manager precision. The decrease in retention time is dependant upon the nature of the probe compound the stationary phase and the mobile phase. A decrease of ~0.18 minutes has been empirically observed for the conditions chosen in this procedure. It is based on the "normal/intended" use of the column heater within the chromatograph.

The effect of column temperature on retention times is given by the following:

$$V_R=V_o*(1+k') \qquad \text{Equation 6:}$$

where $V_o$=the column's void volume and k'=the capacity factor for the analyte.

Figure 10:
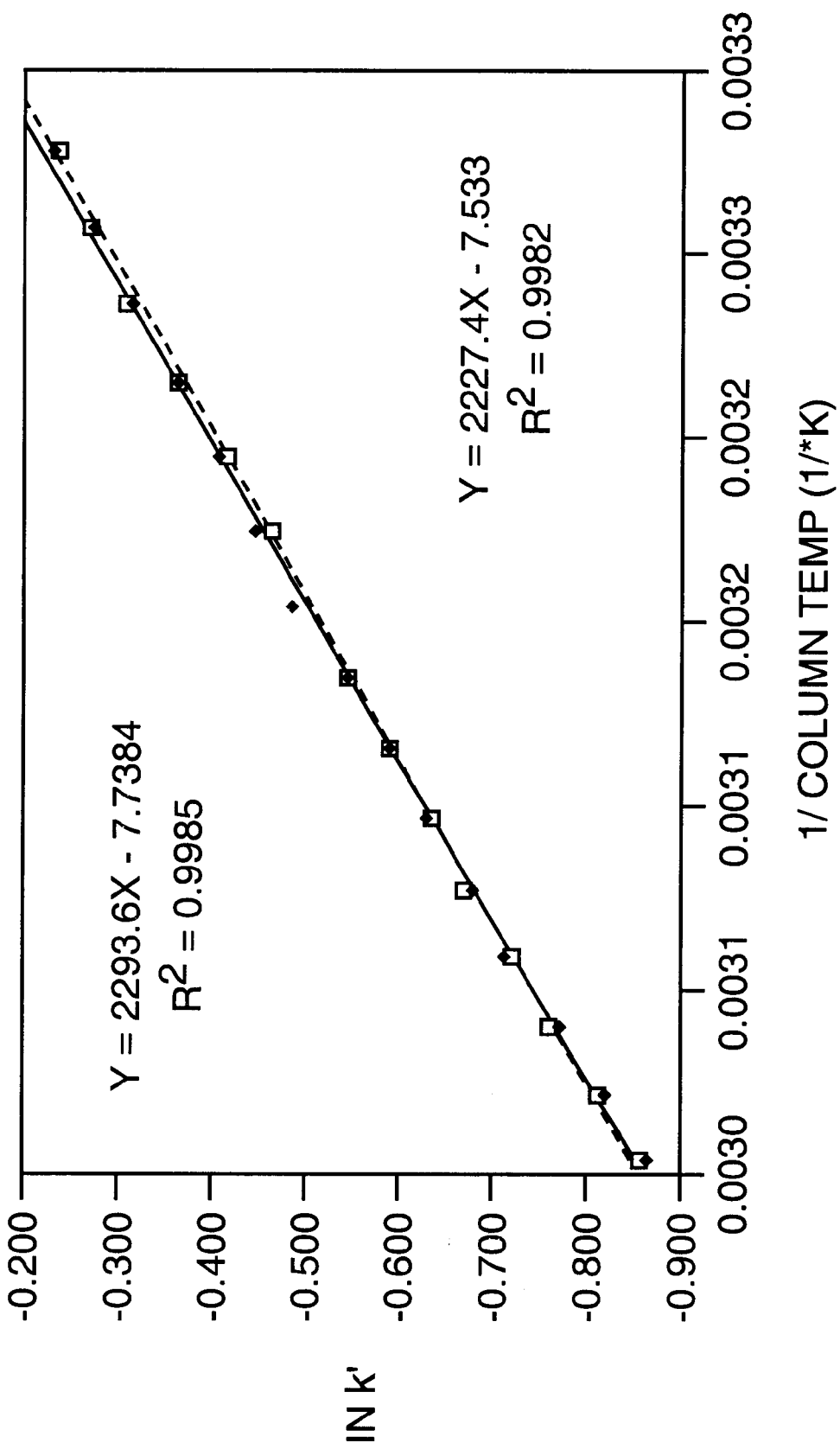
FIG. 10 illustrates the two sets of retention time as a function of column temperature.

The capacity factor is related to the equilibrium constant for the partitioning of the analyte between the stationary phase and mobile phase by Equation 7.

$$k'=K*\theta=C_s*\theta/C_M \qquad \text{Equation 7:}$$

where K=equilibrium constant=$C_S/C_M$ and θ=phase ratio= $V_S/V_o$ with $V_S$ being the volume of stationary phase contained within the column and $V_o$ being the volume of mobile phase contained within the column. The equilibrium constant has the usual thermodynamic dependence upon temperature as given by Equation 8.

$$\ln(K)=\ln k'-\ln\theta=-1/RT*\Delta G° \qquad \text{Equation 8:}$$

where ΔG° is the Gibbs free energy associated with the partitioning of the analyte between the stationary and mobile phases. A plot of lnk' vs. 1/T (°K) is linear with a slope of (−ΔG°/R) and an intercept of lnθ. An example of two sets of retention time measurements as a function of column temperature (from 30° C. to 60° C.) is shown in FIG. 10. While equations 6 and 8 predict a non-linear dependence of retention time with certain temperatures, FIG. 11 demonstrates that there is a reasonable degree of linearity over a short range of temperature.

Figure 11:
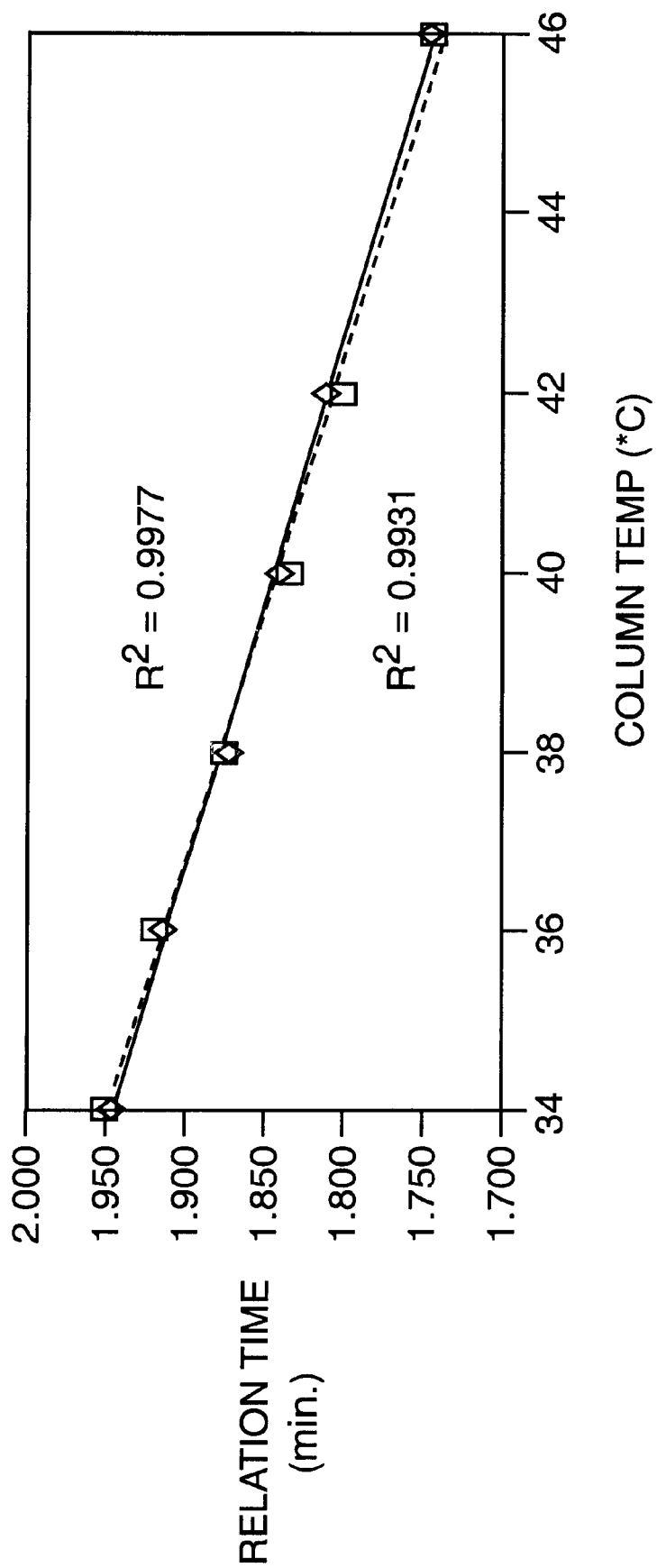
FIG. 11 illustrates a reasonable degree of linearity that occurs over a shorter range of temperatures.

As a result, a simple approach that is amenable to automation, is the verification of column heaters by measuring the shift in retention time for a well-equilibrated system with a column temperature set at 35° C. which is then reset to 45° C. and equilibrated to the new value. This approach as illustrated in FIG. 11.

Although the automated test protocol described in the illustrative embodiment herein is a series of methods that pertain to the installation, operational and performance qualification of chromatography systems it should be appreciated that qualification procedures could be implemented such as to qualify the individual modules of a chromatography system in the event repairs must be done, or the like. Similarly, rather than the need for any operator intervention, qualification could be effected by making the preparation of the chromatography system completely automated.

The foregoing has been a description of an illustrative embodiment of the present invention. The present invention is not to be limited in scope by the illustrative embodiments described which are intended as specific illustrations of individual aspects of the invention, and functionally equivalent methods and components are within the scope of the invention. Indeed, various modifications of the invention, in addition to those shown and described herein will become apparent to those skilled in the art from the foregoing description. Such modifications are intended to fall within the scope of the appended claims

What is claimed:

1. An automated method for qualification of a chromatography system, having a detector, solvent delivery system, sample manager, and column, comprising the steps of:

preparing the chromatography system to ensure that samples, solvents, and column are ready for analysis;

qualifying the detector to ensure operation within specified detection parameters;

qualifying the solvent delivery system to ensure operation within specified solvent delivery parameters;

qualifying the sample manager to ensure operation within specified sample delivery parameters;

utilizing regression analysis to compute performance of accuracy, linearity, and precision of the chromatographic system; and validating performance of the chromatography system based upon said regression analysis.

2. The automated method for qualification of a chromatography system according to claim 1, wherein said chromatography system includes a gradient proportioning system, further including the step of qualifying the gradient proportioning system to ensure operation within specific gradient proportioning parameters.

3. The automated method for qualification of a chromatography system according to claim 1, wherein said chromatography system includes a delay volume, further including the step of qualifying delay volume of the chromatography system to ensure operation within specific delay volume parameters.

4. The automated method for qualification of a chromatography system according to claim 1, wherein said chromatography system includes a column heater, further including the step of qualifying the column heater to ensure operation within specific column temperature parameters.

5. The method of claim 1, wherein said detector is an absorbance detector.

6. The method of claim 1, wherein said detector is a photodiode array detector.

7. The method of claim 1, wherein said detector is a fluorescence detector.

8. The method of claim 1, wherein said detector is a refractive index detector.

9. The method of claim 1, wherein said method for qualification is compliant with FDA regulations relating to electronic signatures and electronic records.

10. The method of claim 9, further including the step of generating a report to confirm compliance of the chromatography system.

11. The method of claim 10, further including the step of reviewing said report to confirm compliance of the chromatography system.

12. The method of claim 10, wherein said report is compliant with Good Laboratory Practice.

13. The method of claim 10, wherein said report is compliant with Good Manufacturing Practice.

14. The method of claim 10, wherein said report is compliant with Good Clinical Practices.

15. The method of claim 10, wherein said report is a hardcopy report.

16. The method of claim 1, wherein said regression analysis generates data that is placed within an Oracle database.

17. An automated method for installation qualification of a chromatography system, comprising the steps of:

storing details of installation data within a Oracle database table;

creating an unique sequence for each record stored in said table;

preventing the deletion of said records; and accessing said data using data objects.

18. An apparatus for use with a computer system, including a central processing unit, and an application program, for qualifying a chromatography system comprised of a plurality of components, each of the plurality of components operating on parameter data and producing output values therefrom, the apparatus comprising:

storage means controlled by the central processing unit and cooperating with the computer system to store the application program;

means for storing predicate rules for detecting invalid data, the predicate rules comprising precondition rules for detecting invalid parameter data and post condition rules for detecting invalid output values generated by one of the plurality of components;

means responsive to the stored application program and to the stored predicate rules for compiling the predicate rules and the application program to generate an executable program module, an executable precondition module and an executable post condition module in a common library; and means controlled by the central processing unit and responsive to the output values for applying the output values to the post condition module to detect invalid output data.

* * * * *